(12) United States Patent
Sol

(10) Patent No.: US 6,231,527 B1
(45) Date of Patent: May 15, 2001

(54) METHOD AND APPARATUS FOR BIOMECHANICAL CORRECTION OF GAIT AND POSTURE

(76) Inventor: Nicholas Sol, 2215 Angel Bluff Ct., Colorado Springs, CO (US) 80919

( * ) Notice: Subject to any disclaimer, the term of this patent is extended or adjusted under 35 U.S.C. 154(b) by 0 days.

(21) Appl. No.: 08/536,086

(22) Filed: Sep. 29, 1995

(51) Int. Cl.[7] .................................................... A61B 5/103
(52) U.S. Cl. ......................... 600/595; 348/157; 348/77; 348/143; 382/100; 382/128; 434/247; 434/252
(58) Field of Search ..................... 348/157, 77, 143; 382/100, 128; 434/247; 600/587, 595

(56) References Cited

U.S. PATENT DOCUMENTS

| | | | |
|---|---|---|---|
| 4,182,316 | * | 1/1980 | Nilsson ................................. 128/782 |
| 4,267,728 | * | 5/1981 | Manley ............................. 128/779 X |
| 4,416,293 | * | 11/1983 | Anderson . |
| 4,600,016 | * | 7/1986 | Boyd ..................................... 128/782 |
| 4,631,676 | * | 12/1986 | Pugh ..................................... 128/782 |
| 4,713,686 | * | 12/1987 | Ozaki . |
| 4,906,193 | * | 3/1990 | McMullen ........................ 128/782 X |
| 5,080,109 | * | 1/1992 | Arme ................................... 128/782 |
| 5,203,346 | * | 4/1993 | Fuhr ................................. 128/782 X |
| 5,249,967 | * | 10/1993 | O'Leary ........................... 434/252 X |
| 5,337,757 | * | 8/1994 | Jain . |
| 5,630,422 | * | 5/1997 | Zanakis ............................ 128/782 X |

OTHER PUBLICATIONS

Feldkamp, Fortschr Med (Feb. 1978) West Germany, Journal Article, (1978).*
Knusel, Schweizz SportMed (Dec. 1985), Switzerland, Journal Article.*

* cited by examiner

*Primary Examiner*—Glenn E. Richman
(74) *Attorney, Agent, or Firm*—John E. Reilly

(57) ABSTRACT

A method and apparatus have been devised for analyzing abnormal conditions of gait and posture and for translating such analysis into biomechanical correction through the utilization of orthotics alone and in combination with other measures and which includes a walking platform upon which a patient can stride, video cameras directed at the patient including a frontal camera, lateral camera, overhead camera and lower rear camera, mirrors to produce reflected images of the patient from selected of the cameras, and a closed circuit television for simultaneously displaying images of the patient when striding on the walking platform; and such information is coordinated with more traditional diagnostic measures for determining or sensing ground reactive and weight-bearing forces on the feet both when static and during ambulation to produce an accurate prescription through the use of orthotics alone and in combination with other measures.

17 Claims, 2 Drawing Sheets

METHOD AND APPARATUS FOR BIOMECHANICAL CORRECTION OF GAIT AND POSTURE

BACKGROUND AND FIELD OF INVENTION

This invention relates to a method and apparatus for alleviating chronic musculoskeletal pain, especially lower back pain; and more particularly relates to a novel and improved apparatus for the biomechanical correction of gait and posture.

Human walking is a marvel of engineering. Few animal species are capable of bipedal locomotion; none walk with as much ease or efficiency as we do. When we walk, we use much less direct muscle energy than previously thought. In fact, EMG analysis has shown that the vast majority of muscle activity during walking is occurring in the swing limb. New research has demonstrated that the support limb is primarily a passive structure that our body simply moves over as we progress forward. This research has shown that normal human walking efficiently uses gravity, momentum and the elastic energy return of the spinal structures caused by counter-rotating shoulder and pelvis.

Although primarily a passive structure, our feet are the body's foundation during standing and walking and are the only parts of our bodies to interact with the ground. Epidemiologists have studied the incidence of both common back problems and common foot problems in both developed and undeveloped societies. They have found a direct relationship between the hard, flat, unforgiving floor or ground surfaces and the increased incidence of common foot and back problems.

Normal human cadence is 90–120 steps per minute. This translates into 5400–7200 steps per walking hour. Each foot, in turn, accepts, transfers then propels the body and weight forward. When the various mechanisms in the foot begin to fail, the effects on the body are predictable. With the loss of functional symmetry, the various muscles, tendons, ligaments, joints, etc. involved in posture and locomotion undergo repetitive motion injury caused when one side works too hard while the other words too little. Although these events are individually small, they are magnified by the effects of repetition.

Although many patients with gait abnormalities experience pain in the foot and/or ankle, many more do not. In these patients, the only symptoms of abnormal gait are their postural pains. For example:

Leg: Cramps, shin splits, growing pains, etc.
Knee: Joint pain, ligament strain, etc.
Hip: Joint pain, ligament strain, etc.
Back: Low back pain, SI pain, sciatica disc pain, facet syndrome, muscle spasm, fibromyalgia, myofascial pain, etc.
Neck: Disc pain, trigger points, muscle spasm, muscle tension, headache, myofascial pain, fibromyalgia, etc.
Shoulder: Muscle spasm, trigger points, myofascial pain, fibromyalgia, etc.

In the past, problems associated with gait and posture abnormalities have been solved using various techniques including surgery, acupuncture, acupressure, pain relief medicine, etc. However, attempts to solve those problems using one of the aforementioned techniques do not always effect a permanent relief or cure, particularly where the underlying cause of such problems has to do with abnormalities in gait and posture. It has been common practice for podiatrists to prescribe orthotics for the correction of improper foot mechanics, undue pressure in certain regions of the foot or unbalanced pressure between the feet. However, to the best of my knowledge, no one has devised an effective, accurate system or procedure to correct for abnormalities in gait and posture in order to alleviate chronic musculoskeletal pain of the types described. For example, PCT Application WO94/20020 published Sep. 15, 1994 is directed to a method and apparatus for recording characteristics of a person's foot through the utilization of a combination of video images from the underside, front, rear and side of the feet and multiplexing those images to provide a single combined signal which can be analyzed geometrically to ascertain the characteristics of the person's feet.

European Patent EP074231 discloses an apparatus for conducting dynamic podologic studies with the use of cameras and mirror. U.S. Pat. No. 5,299,454 to D. Fuglewicz et al is directed to a continuous foot-strike measuring system and method which broadly suggests the use of video analysis but is concerned more with the use of two force plates in tandem in combination with sensor elements to sense where the force is applied. U.S. Pat. No. 4,416,293 to B. V. Anderson et al discloses a method and apparatus for recording gait analysis in podiatric design and treatment with the use of video and sound recording. U.S. Pat. No. 4,813,436 to J. C. Au is directed to a motion analysis system employing various operating modes through the use of a pair of cameras, strobe light and pressure mat. Other representative patents are U.S. Pat. Nos. 3,894,437 to J. L. Hagy et al, 4,267,728 to M. T. Manley et al, U.S. Pat. No. 4,598,717 to A. Pedotti, U.S. Pat. No. 4,600,016 to T. L. Boyd et al and German Patent DE4027317. Prior art systems fall short of providing the necessary diagnosis and video analysis of the whole body of each patient to prescribe the proper orthotics or biomechanical correction of gait and posture in order to alleviate chronic pain of the type described and overcome repetitive motion injury resulting from abnormalities in gait and posture.

SUMMARY OF THE INVENTION

It is an object of the present invention to provide for a novel and improved method and apparatus for alleviating chronic musculoskeletal pain and particularly lower back pain.

Another object of the present invention is to provide for a novel and improved apparatus for alleviating pain through the biomechanical correction of gait and posture of an individual; and further wherein such biomechanical correction can be made through the use of orthotics alone or in combination with other measures.

It is a further object of the present invention to provide for a novel and improved method and apparatus for biomechanically correcting abnormalities in gait and posture utilizing a highly simplified, accurate method of video analysis which can be coordinated with the measurement of ground reactive and weight-bearing forces on the feet to prescribe orthotics which will biomechanically correct any abnormalities in gait and posture.

In accordance with the present invention, there has been devised a novel and improved apparatus for analyzing abnormal conditions of gait and posture which comprises a walking platform upon which a person can stride, a plurality of video cameras directed at the whole body of the patient including a frontal camera directed substantially horizontally at the patient, a lateral camera directed substantially at one side of the patient, and an overhead camera directed downwardly from above the patient, means for activating the cameras simultaneously to produce images of the patient striding on the platform, and means for recording the images for analysis of abnormal conditions in gait and posture. In addition, mirrors are provided in facing relation to selected of the cameras in order to produce reflected images of the patient including a rear mirror disposed behind the platform and a lateral mirror disposed to one side of the platform.

The method for analyzing abnormal conditions of gait and posture in a patient according to the present invention comprises the steps of providing a walking platform upon which the patient can stride, placing a plurality of video cameras directed at the whole body of the patient including a frontal camera, lateral camera and overhead camera and simultaneously producing images of the patient when striding in place from the front, side and above the patient, and multiplexing the images onto a screen and analyzing a succession of the images over a predetermined time interval. Preferably the method further includes the step of placing mirrors at the rear and side of the walking platform in facing relation to the frontal camera and lateral camera, respectively, and simultaneously producing direct and reflected images of the patient when striding. The method is further characterized by simultaneously producing images of the patient when striding barefoot and when striding in shoes as well as to employ a rear camera behind the walking platform to produce images of the patient's feet and lower limbs when striding either barefoot or in shoes and multiplexing with the other images produced.

The above and other objects of the present invention will become more readily appreciated and understood from a consideration of the following detailed description of preferred and modified forms of the present invention when taken together with the accompanying drawings in which:

DETAILED DESCRIPTION OF PREFERRED EMBODIMENT

Figure 2:
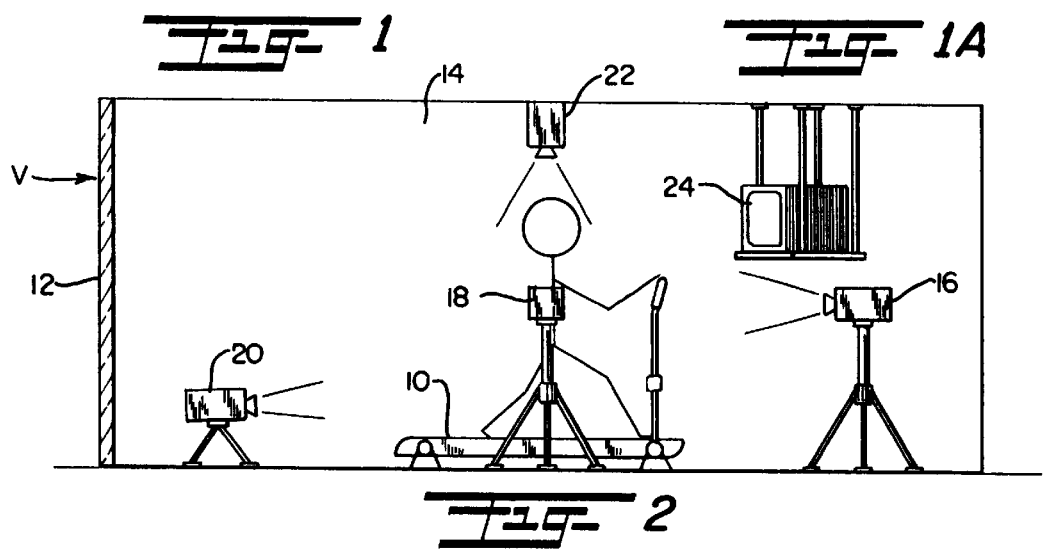
FIG. 2 is a diagrammatic side view of the preferred form of method and apparatus for video imaging of the patient in an ambulatory state.
Figure 3:
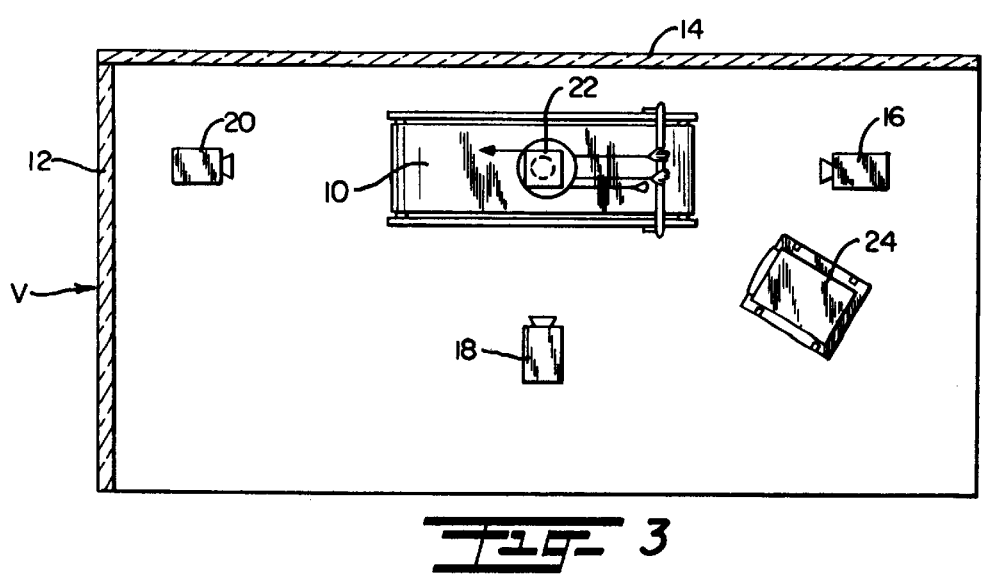
FIG. 3 is a diagrammatic overhead view of the preferred form of method and apparatus for video imaging of the patient in an ambulatory state.

Referring in more detail to the drawings, a preferred form of video analysis system V is illustrated in FIGS. 2 and 3 and is comprised of a treadmill or other walking platform 10 placed in a corner of a room. A full-length mirror 12 is placed on a rear vertical wall behind the treadmill 10 and a lateral full-length mirror 14 is placed on a side wall to traverse the length of the treadmill 10. A combination of four video cameras is employed including a frontal camera 16, lateral camera 18 disposed on one side opposite to the mirror 14, a lower rear camera 20 directed forwardly and upwardly at the rear of the treadmill 10, and an overhead camera 22 disposed in the ceiling of the room directly above and in centered relation to the treadmill belt. Each of the cameras is adjustable for each patient. A video screen or closed circuit television 24 may be stationed at any convenient place in the vicinity of the system to produce video images in response to the video signals received from the four cameras and, in a conventional manner, is of a type capable of displaying the images in slow motion and of multiplexing the images to permit simultaneous viewing of the images from each camera. When a patient is either standing or walking in place on the treadmill, it is possible to observe the patient simultaneously from four different angles; and through frame-by-frame analysis and electronic split screen, or multiplexing, it is possible to analyze the functional and anatomical relationships of the limbs, trunk, head and neck during gait, paying particular attention to motion, symmetry, timing and efficiency of gait and posture. Slow motion video analysis provides a most accurate and comprehensive look at the way one's body moves when walking. Subtle functional imbalances become visible and indicate the sites of both primary malfunction and chronic overuse due to repetitive motion injury. Utilization of the mirrors 12 and 14 at the rear and one side of the treadmill enable the frontal camera 16 and lateral camera 18, respectively, to produce a direct image and reflected image on the screen. The reflected image will be displaced somewhat from the direct image and can be controlled by adjustment of the camera position and angle with respect to the patient. In split screen analysis, therefore, it is possible to view six images of the patient at one time. For example, during slow motion video gait and posture analysis, the frontal direct and reflected images permit observance of head tilt, shoulder tilt, torso bend, pelvic tilt; the lateral direct and reflected images permit viewing of head tilt, cervical spine hip extension, stride length; the lower rear images directed at the ankle and foot permit observance of early or late heel lift, propulsion, initial swing; and overhead or transverse images permit observance of counter-rotation of pelvis, shoulder rotation, head tilting, trunk bending not otherwise perceivable through the first three camera images.

The following Tables I, II, III and IV illustrate and are representative of the conditions to be observed and, where necessary, to be corrected from an examination of the images produced by the frontal, lateral, rear and transverse cameras of a person walking at a normal gait on the treadmill. In fact, the Tables may be used as checklists for the podiatrist or other person examining a patient to note any abnormal conditions both during barefoot treadmill walking and shod treadmill walking. In a manner to be described, this information will be correlated with information obtained of weight bearing and ground reactive forces on the feet of a person standing at rest and peak pressures on the feet during ambulation.

TABLE I

| FRONTAL | | | |
| --- | --- | --- | --- |
| Rhythmic | [ ]Y | [ ]N | |
| Bouncy | [ ]Y | [ ]N | |
| Head Tilt | [ ]L | [ ]R | [ ]None |
| Shoulder Tilt | [ ]L | [ ]R | [ ]None |
| Dec Arm Swing | [ ]L | [ ]R | [ ]Symmetric |
| Torso Bend | [ ]L | [ ]R | [ ]None |
| Pelvic Tilt | [ ]L | [ ]R | [ ]None |
| Limb Abduct | [ ]L | [ ]R | [ ]None |
| Limb Adduct | [ ]L | [ ]R | [ ]None |
| FF Load (L) | [ ]Varus | [ ]Valgus | [ ]Flat |
| FF Load (R) | [ ]Varus | [ ]Valgus | [ ]Flat |
| Comments: | | | |

TABLE II

LATERAL

| | | | |
|---|---|---|---|
| Head Tilt | []Front | []Back | []None |
| Cervical Spine | []Flex | []Ext | []Rectus |
| Lumbar Spine | []Flex | []Ext | []Rectus |
| Hip Extension (L) | | | |
| Hip Extension (R) | | | |
| Stride Length | []Sym | []Asym | |
| | []L | []R | Longer |
| Heel Knee | []L | []R | |
| Toe Off (L) | []MTP | []Hallux | []Other |
| Toe Off (R) | []MTP | []Hallux | []Other |
| 1st MTP Motion (L) | | | |
| 1st MTP Motion (R) | | | |
| Comments: | | | |

TABLE III

REAR

| | | | |
|---|---|---|---|
| Early Heel Lift | []L | []R | []None |
| Late Heel Lift | []L | []R | []None |
| Propulsion (L) | []Medial | []Lateral | []Flat |
| Propulsion (R) | []Medial | []Lateral | []None |
| Toe Off (L) | []MTP | []Hallux | []Other |
| Toe Off (R) | []MTP | []Hallux | []Other |
| Initial Swing (L) | []Abd | []Add | []Straight |
| Initial Swing (R) | []Abd | []Add | []Straight |
| Comments: | | | |

TABLE IV

TRANSVERSE

| | | | |
|---|---|---|---|
| Torso Bend | []L | []R | []None |
| Torso Attitude | []L | []R | []Straight |
| Clockwise | | | |
| Counterclockwise | | | |
| Arm Swing (L) | []Coord | []Uncoord | |
| Arm Swing (R) | []Coord | []Uncoord | |
| Arm Swing | []Symm | []Asymm | |
| | []L | []R | []Greater |
| Comments: | | | |

Figures 1, 1A:
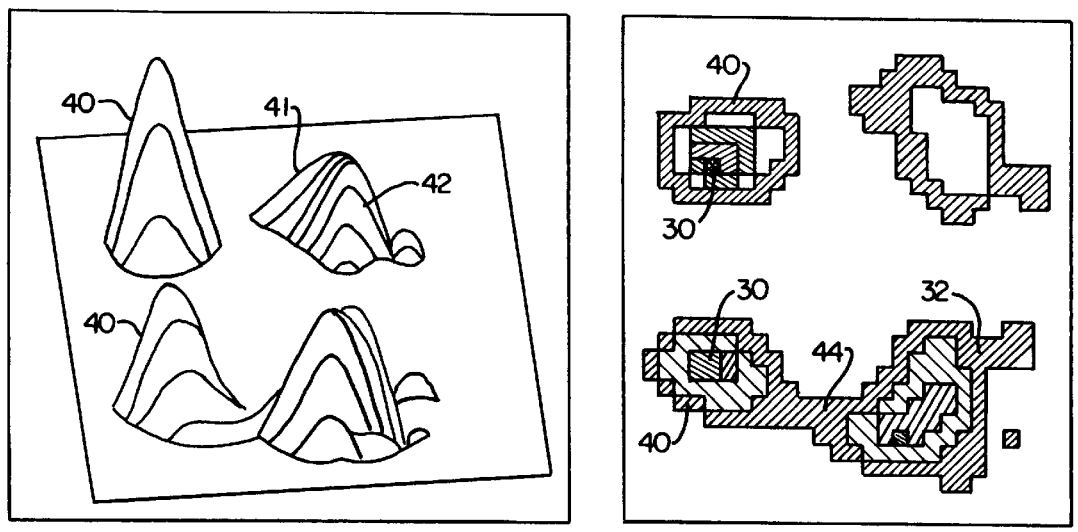
FIGS. 1 and 1A are somewhat diagrammatic views illustrating static stance testing of the foot.

In relation to the above Tables, FIGS. 1 and 1A are somewhat diagrammatic views of static stance ground reactive and weight-bearing forces on each foot when the patient is required to stand on a pressure mat containing pressure transducers which transmit signals to a computer. A suitable pressure mat for this purpose is manufactured and sold by Tekscan, Incorporated of Boston, Mass. FIG. 1 is an image of ground reactive forces which demonstrates that the forces transmitted through the left foot (top) are greatest in the heel region 40 but there are also additional peaks in the lateral forefoot 41 and central forefoot region 42. The forces transmitted through the right foot (bottom) show an almost uniform pressure distribution with the exception of high concentration in the heel region 40. Referring to FIG. 1A of the weight-bearing force images, it will be seen that there is asymmetry in the overall patterns; i.e., the left foot has a different footprint than the right. The left foot (top) demonstrates abnormally high pressure concentration in the heel region 40 whereas the right foot image (bottom) does not demonstrate the same concentration of weight which may be explained by the overall wider area of distribution especially in the arch region 44. The amount of pressure in pounds per square inch is represented by the gradations in shading with the shaded areas 30 representing the highest pressure points, shaded areas 31 representing intermediate pressure levels and shaded areas 32 representing lowest pressure levels.

In the method according to the present invention, the patient is instructed to stand on the pressure mat to test static stance ground reactive forces and weight-bearing forces as described. The patient is then placed on the treadmill without shoes or socks and instructed in emergency shut-down procedures. The treadmill is started and the patient begins walking on the moving belt. Walking speed is adjusted using the variable speed control of the treadmill to establish the usual and comfortable pace and stride for the patient. Since both stride and leg length vary from individual to individual, the variable speed adjustment on the treadmill is used to establish a cadence of 90–120 steps per minute. The treadmill surface is level. Once established, the treadmill speed is noted and the video capture process begins.

The first part of the process captures global or whole body mechanics during barefoot gait. The frontal camera captures direct whole body frontal and reflected whole body rear images. Next, the rear camera which is mounted slightly behind the treadmill at platform level and angled upwardly captures direct rear images. The lateral camera captures direct right lateral and reflected left lateral images. Finally, the overhead camera captures direct overhead images. Quadraplex images from the four cameras are captured. Elapsed time is approximately 60 to 90 seconds.

The patient continues walking at the same speed while the second part of the process captures local mechanics; i.e., close-up lower extremities during barefoot gait. The frontal and lateral cameras are zoomed and refocused on the lower extremities. Images are then captured from the frontal camera including direct frontal and reflected rear views of the lower extremities. Next, images are captured from the lateral camera including direct and reflected lateral views. Finally, the quadraplex images are captured with an elapsed time of approximately 30 to 60 seconds. The treadmill is stopped and then the patient puts on shoes and socks.

In the third part of the process, global or whole body mechanics are captured during shod gait. This is used with the images produced in the first and second parts for diagnostic purposes and for comparison to the final video images captured with shoes and orthotics. The treadmill is started and the patient begins walking and the speed adjusted to the same value as for the first part, the video capture process being repeated as done for the first part of the processes. These images may be reviewed with the patient using the jog and shuttle features of the system for slow motion, frame-by-frame and freeze frame analysis of mechanics, range of motion and repetitive motions.

Following the treadmill test phases one to three described above, test orthotics are fabricated and modified to normalize ground reactive forces during ambulation. Orthotics are initially fabricated utilizing layers of closed cell foam which are heated and placed on a large block of medium density foam rubber. The patient places two athletic socks on one foot and in a seated position with the femur straight ahead and the knee flexed until the tibia is 90° to the ground, the foot is placed onto the layers of heated close cell foam and manual pressure applied by the operator on the distal femur to compress the foot into the foam. Typically, this position is maintained for approximately two minutes and the foot is lifted. Following removal of the layers, the patient then places two socks on the other foot and the process is repeated. Both cell foam layers are allowed to harden and cool. Negative impressions of both feet are made in the standard manner and are sent to the orthotic lab with the patient's prescription for fabrication of the permanent orthotics.

Figure 4A:
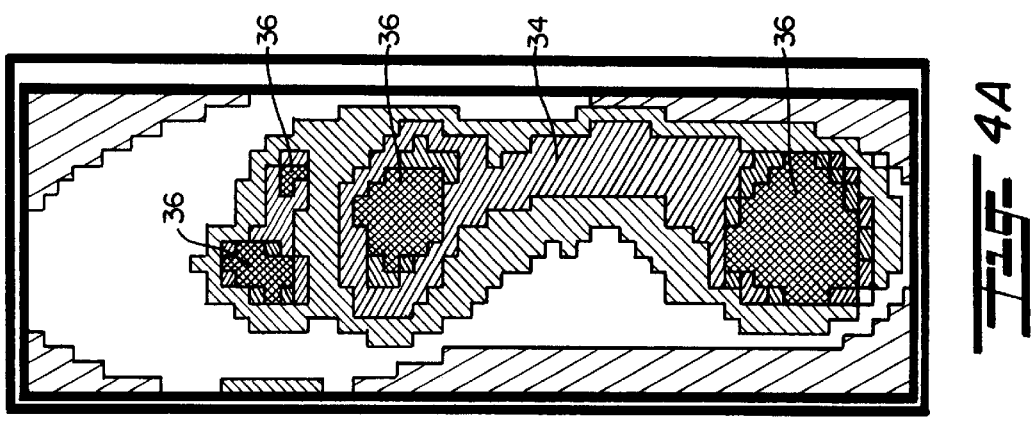
FIGS. 4 and 4A represent printouts of the left and right feet, respectively, which illustrate computer analysis of the timing, degree and amplitude of pressure over different regions of each foot without orthotics.
Figure 4:
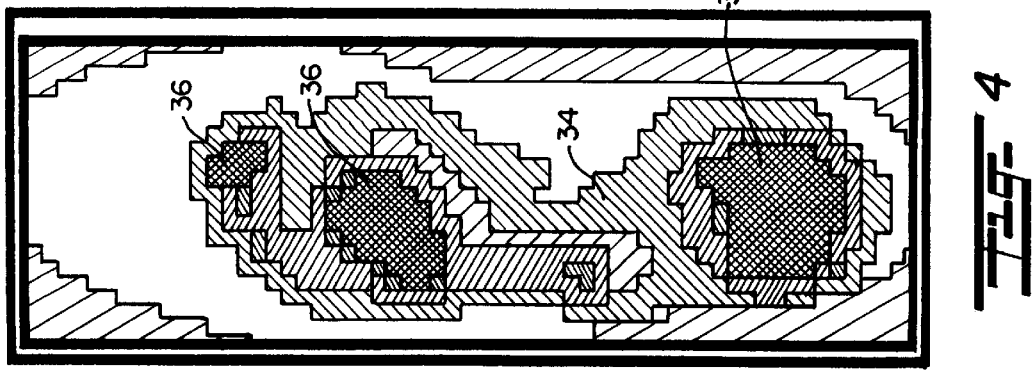

Pressure point analysis of the feet may be carried out in a number of ways. One preferred method is utilization of F-Scan manufactured and sold by Tekscan, Incorporated of Boston, Massachusetts which is a computerized evaluation of pressure and time utilizing in-shoe sensors. Although not shown, the in-shoe sensors are extremely thin, flexible plastic sheets made in different sizes to conform to the outline of each foot and containing pressure transducers which transmit signals of the ground reactive forces to a computer, not shown. However, FIGS. 4, 4A and 5, 5A illustrate the ground reactive forces which are graphically portrayed on the computer screen, the shaded areas 34 and 35 illustrating the lower intermediate pressure points, respectively, and darker shaded areas 36 the higher pressure points. The in-shoe sensors are placed in the patient's shoes and, wearing shoes and socks, the sensors are calibrated for the patient's weight and the calibration file saved for further testing. Dynamic force data or pressure point analysis is then collected by the computer as the patient walks over a limited distance of approximately 15 to 20 yards. The characteristic peak force patterns without orthotics are printed as illustrated in FIGS. 4 and 4A and are later used for base-line documentation and comparison to final patterns with the orthotics in place.

Figure 5A:
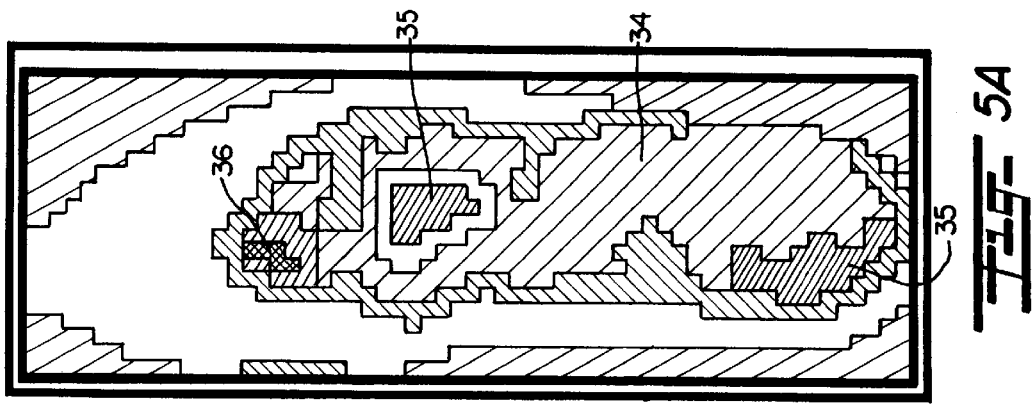
FIGS. 5 and 5A are views corresponding to those of FIGS. 4 and 4A but with the use of orthotics on the left and right feet, respectively.
Figure 5:
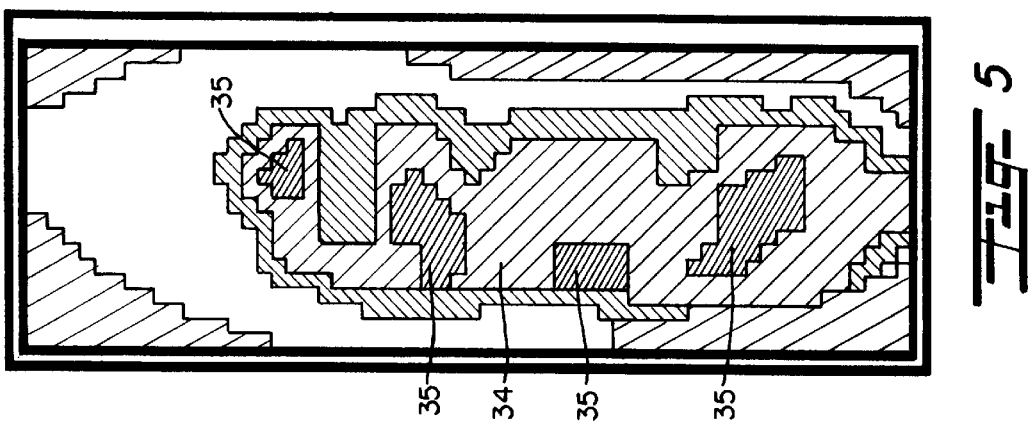

The molded layers of closed cell foam previously custom molded as described are converted into test orthotics by grinding away excess from the sides and bottom of the layers. The test orthotics are placed into the patient's shoes and the in-shoe sensors are placed over the test orthotics and the patient places his feet into the shoes. The sensors are recalibrated using the previously saved calibration file and once again dynamic force data is collected, as shown in FIGS. 5 and 5A. At this point, the characteristic peak force patterns are not printed but are used to direct the initial modification to the test orthotics. After modification, the orthotics are replaced in the shoe and another in-shoe sensor test conducted using the previously noted F-Scan procedure. This may be repeated a number of times until all areas of peak pressure are reduced, neutralized or no further changes are observed in the characteristic peak pressure patterns. The final patterns are printed for documentation and for comparison to base-line patterns.

Once completed, the test orthotics are examined to determine what modifications were made in order to complete the orthotic prescription which is sent with the negative impression molds to the orthotic lab for fabrication of the permanent orthotics. Final video images are captured of the patient walking with completed test orthotics in both shoes on the treadmill at the same speed as used without the orthotics. These images are reviewed with the patient and compared with the images obtained in part three of the initial treadmill phase of testing as earlier described Throughout the modification procedure, the podiatrist or other operator of the test will modify the test orthotics based not only on the peak pressure illustrations graphically displayed on the computer but in light of abnormal conditions detected from the static stance test and video imaging or treadmill tests.

The following working examples serve to illustrate diagnosis and treatment of patients for chronic pain or abnormal conditions through orthotic prescription alone or in combination with other remedies:

EXAMPLE 1

A patient with complaints of chronic back pain is examined and found to have an adequate range of motion (60°) in the 1st metatarsalphalangeal joint (MTP joint) when non-weight bearing. When walking, the video demonstrates that there is a significant restriction of motion with a total range of only 30° when walking. This indicates functional Hallux Limitus and has a proportional effect on hip extension. In this patient, there may only be 5° of hip extension on the effected side of single limb support. Consequently, the Psoas muscle (a hip flexor) must overwork to not only flex the hip and lift the limb but also accelerate the limb because it is moving too slowly due to the lack of acceleration into swing from gravity. This patient might lean away from the effected limb at toe off to help elevate it and relieve the stress to the Psoas. Since normal human cadence is 90–120 steps per minute when walking, this becomes a minimum of 2700 repetitions per walking hour per side. Therefore, he leans only to one side repetitively when walking and causes overuse of some of the involved muscles, joints and abnormal and asymmetric loads applied to the facets and intervetebral discs. Recognition of this abnormality generally would dictate the use of a first ray cut-out, commonly referred to as a "Kinetic Wedge", in designing the test orthotics.

EXAMPLE 2

A patient with a complaint of abnormal gait secondary to a stroke is examined and determined to have spastic gastroc equinus deformity on the affected side. Slow motion video examination of his gait and posture demonstrate that he has a spastic left hemiplegia gait style. His left heel does not contact the support surface at any time in the gait cycle. His left knee does not maximally extend during the support phase of gait and he demonstrates a right to left torso bend during left single limb support secondary to a functionally short left leg. F-Scan analysis of static stance demonstrates no ground reactive forces or weight-bearing forces on the affected heel. He is fitted with an ankle foot orthosis which is modified according to F-Scan analysis of dynamic peak pressures occurring during walking (similar to the method used in modifying test orthotics) which holds his ankle in neutral thereby allowing his heel to contact the support surface at the beginning of contact phase. If the ankle foot orthosis does not maintain the ankle in neutral, the patient may be referred for corrective surgery to length the achilles tendon after which he would still require the use of the ankle foot orthosis to maintain ankle neutral.

EXAMPLE 3

A patient with a complaint of achilles tendonitis is examined and determined to have a tight gastroc. Slow motion video examination of his gait and posture demonstrate an early heel lift on the affected side. The F-Scan evaluation of static stance shows predominant ground reactive forces and weight-bearing forces transmitted through the forefoot of the affected side. F-Scan analysis of dynamic peak pressures occurring during walking demonstrate that there is minimal pressure of short duration on the affected heel. Treatment for this problem includes a heel lift on the affected side.

EXAMPLE 4

A patient with a complaint of metatarsalgia is examined and found to have bilateral gastroc-soleus ankle equinus and Function Hallux Limitus. Slow motion video analysis of gait and posture demonstrate early heel lift bilaterally with a bouncy type gait, decreased dorsiflexion of the 1st MTP joint at propulsion bilaterally with propulsion off the second and third metatarsal heads bilaterally. F-Scan analysis of static stance demonstrates predominant ground reactive forces and weight-bearing forces transmitted through the forefoot bilaterally. F-Scan analysis of dynamic peak pressures occurring during walking demonstrate minimal pressures on the heels bilaterally with discrete areas of abnormally high pressure under the second and third metatarsal heads and great toes bilaterally. Test orthotics are fabricated and modified according to the process of the present invention which correct the abnormal forefoot pressures but do not increase the pressures on the heels bilaterally. Bent knee and straight knee stretches are recommended to stretch both the gastroc and soleus tendons and allow the heel to bear more weight in addition to the use of orthotics.

From the foregoing, it will be appreciated that a novel and improved method and apparatus have been devised for alleviating chronic musculoskeletal pain and particularly chronic lower back pain in a highly dependable and accurate manner which correlates the detection and analysis of abnormalities in gait and posture with ground reactive and weight-bearing forces on the feet through orthotic prescription alone or in combination with other measures. In this relation, while a preferred method and apparatus are herein set forth and described, it will be apparent that various modifications and changes may be made therein without departing from the spirit and scope of the present invention as defined by the appended claims.

I claim:

1. Apparatus for analyzing abnormal conditions of gait and posture comprising:

a walking platform upon which a patient can stride;

a plurality of video cameras directed at the whole body of the patient from different vantage points including a frontal camera directed horizontally at the patient, a lateral camera directed at one side of the patient, and an overhead camera directed downwardly from above the patient; means for activating said frontal, lateral and overhead cameras to produce multiple images of the patient striding on said platform;

means for simultaneously displaying a succession of said multiple images from said different vantage points on a common screen for analysis of abnormal conditions in gait and posture; and wherein sensor means are inserted in shoes worn by patient for sensing ground reactive and weight-bearing forces the feet of said patient during ambulation.

2. Apparatus according to claim 1, wherein mirrors are provided in facing relation to selected of said cameras to produce reflected images of said patient when said selected of said cameras are activated.

3. Apparatus according to claim 2, wherein said mirrors include a rear mirror disposed behind said platform in facing relation to said frontal camera and a lateral mirror disposed to one side of said platform opposite to said lateral camera.

4. Apparatus according to claim 1, wherein said recording and display means are characterized by multiplexing said images onto said screen in real time and in slow motion.

5. Apparatus according to claim 1, wherein a rear camera is located behind said walking platform to produce images of the patient's feet and lower limbs when striding.

6. Apparatus according to claim 1, wherein means are provided for modifying ground reactive and weight-bearing forces on each foot of said patient in response to the abnormal conditions analyzed by said recording means.

7. Apparatus according to claim 6, wherein said means include orthotics.

8. The method for analyzing abnormal conditions of gait and posture in a patient for alleviating lower pain with the use of corrective orthotics comprising the steps of:

providing a walking platform upon which the patient stride;

placing a plurality of video cameras directed at the whole body of the patient from different vantage points including a frontal camera, lateral camera and overhead camera and producing multiple images of the patient when striding in place from the front, side and above the patient;

multiplexing said multiple images onto a common screen and analyzing a succession of said multiple images over a predetermined time interval for determining abnormal conditions in gait and posture; and repetitively sensing ground reactive forces on each foot of the patient when striding, modifying the ground reactive and weight-bearing forces by placing orthotics in each shoe of the patient, repetitively sensing ground reactive forces on each foot and modifying the orthotics for each foot to correct the abnormal conditions analyzed.

9. The method according to claim 8, including the step of placing mirrors at the rear and side of said walking platform in facing relation to said frontal camera and said lateral camera, respectively, and simultaneously producing direct and reflected images of the patient when striding.

10. The method according to claim 8, including the step of placing a camera behind said walking platform and producing images of the patient's feet and lower limbs when striding.

11. The method according to claim 8, including the step of sensing ground reactive and weight-bearing forces on the feet of said patient when static.

12. The method according to claim 11, including the step of sensing ground reactive and weight-bearing forces on the feet of the patient when striding.

13. The method according to claim 12, including the step of modifying ground reactive and weight-bearing forces on each foot of the patient to correct for the abnormal conditions analyzed.

14. The method according to claim 8, characterized further by simultaneously producing images of the patient when striding barefoot and when striding in shoes.

15. The method according to claim 8, including the step of adjusting said frontal, lateral and overhead cameras in relation to each patient.

16. The method according to claim 9, including the step of adjusting said frontal and lateral cameras to simultaneously produce direct and reflected images by each of said frontal and lateral cameras when the patient is striding.

17. The method according to claim 8, wherein said walking platform is a powered treadmill and including the step of adjusting the speed of said treadmill to match the normal cadence of the patient when striding.

* * * * *